United States Patent [19]
Katzman

[11] Patent Number: 5,944,670
[45] Date of Patent: Aug. 31, 1999

US005944670A

[54] BREATH TEST FOR THE DIAGNOSIS OF BACTERIAL INFECTION

[75] Inventor: Daniel E. Katzman, Jerusalem, Israel

[73] Assignee: Oridion Medical Ltd., Jerusalem, Israel

[21] Appl. No.: 08/759,340

[22] Filed: Dec. 2, 1996

[51] Int. Cl.[6] .................................................. G01N 38/53
[52] U.S. Cl. .......................................... 600/543; 600/529
[58] Field of Search .................................... 600/543, 529, 600/532, 530, 300

[56] References Cited

U.S. PATENT DOCUMENTS

| | | |
|---|---|---|
| Re. 33,493 | 12/1990 | Lee et al. . |
| 4,755,675 | 7/1988 | Rosenfeld et al. . |
| 4,830,010 | 5/1989 | Marshall . |
| 5,300,859 | 4/1994 | Yatsiv et al. . |
| 5,317,156 | 5/1994 | Cooper et al. . |
| 5,394,236 | 2/1995 | Murnick . |
| 5,629,167 | 5/1997 | Ratti ......................................... 435/7.9 |

FOREIGN PATENT DOCUMENTS

| | | |
|---|---|---|
| 1312114 | 12/1992 | Canada . |
| WO 90/00061 | 6/1989 | WIPO . |
| WO 92/22819 | 12/1992 | WIPO . |

OTHER PUBLICATIONS

Brown, P. "Can You Catch a Heart Attack?", *New Scientist,*, pp. 39–42, Jun., 1996.

Valkonen, et al., "Proteinase Associated with *Chlamydia Pneumoniae*", Abstracts from Third European Chlamydia Meeting, Sep., 1996.

Gaydos, et al., "*Chlamydia Pneumoniae* Infections in Macrophages and Coronary Artery Endothelial Cells", Abstracts from Third European Chlamydia Meeting, Sep., 1996.

Ong, et al., "*Chlamydia Pneumoniae* in Vascular Tissue", Abstracts from Third European Chlamydia Meeting, Sep., 1996.

Juvonen, et al., "Detection of *Chlamydia Pneumoniae* in Human Non–Rheumatic Stenotic Aortic Valves", Abstracts from Third European Chlamydia Meeting, Sep., 1996.

Blasi, et al., "A Possible Role for *Chlamydia Pneumoniae* Infection in Acute Myocardial Infarction Onset", Abstracts from Third European Chlamydia Meeting, Sep., 1996.

Prosser, et al., "Rapid, Automated Analysis of $^{13}C$ and $^{18}O$ of $CO_2$ in Gas Samples By Continuous–Flow Isotope Ratio Mass Spectrometry", *Biol. Mass Spectrom.*, 20:724–730 (1991).

Haisch et al., "Biomedical Application of an Isotope Selective Nondispersive Infrared Spectrometer for $^{13}Co_2$ and $^{12}CO_2$ Concentration Measurements In Breath Samples", Isotopenpraxis–Isotopes in Environmental and Health Studies, 1994.

Cunningham, et al., "Direct Demonstration of *Chlamydia Pneumoniae* and *Helicobacter Pylori* in Coronary Heart Disease", Abstracts from Third European Chlamydia Meeting, Sep., 1996.

Thomsen, Et Al., "Chlamydial Infection in reactive Arthritis with Special reference to *Chlamydia Pneumoniae*", Abstracts from Third European Chlamydia Meeting, Sep., 1996.

*Primary Examiner*—Robert L. Nasser
*Attorney, Agent, or Firm*—Fish & Neave; Jeffrey H. Ingerman; Joel Weiss

[57] ABSTRACT

A breath test for diagnosing the presence of Chlamydia species, such as *Chlamydia pneumoniae*, in a subject is described. The method of diagnosing Chlamydia species in a subject is performed as follows. First, a safe and effective amount of a substrate, preferably appropriately labelled, is administered to the subject. Second, the exhaled breath of the subject is analyzed to detect the concentration of a cleavage product or products, produced when an enzyme from Chlamydia bacteria cleaves the substrate. The presence of the cleavage product or products indicates a positive diagnosis of Chlamydia species in the subject. A breath test kit is also described. Such a breath test kit would include an item or items necessary for performing at least one of the methods of diagnosing Chlamydia species in a subject. For example, such a breath test kit could include a substrate to be administered to the subject.

16 Claims, No Drawings

5,944,670

BREATH TEST FOR THE DIAGNOSIS OF BACTERIAL INFECTION

FIELD AND BACKGROUND OF THE INVENTION

The present invention relates to a breath test for the diagnosis of bacterial infection and, more particularly, to a breath test for the diagnosis of infection by Chlamydia species.

Chlamydia species are bacteria which are responsible for a number of different infections in humans. *Chlamydia trachomatis* is a sexually transmitted disease. Recently, *Chlamydia pneumoniae* has been implicated in coronary heart disease, specifically in the development of atheroma, which is diseased tissue that can block the arteries, potentially leading to a myocardial infarction. Evidence of such an involvement has been growing and includes the detection of DNA from *Chlamydia pneumoniae* in samples of coronary tissue taken from patients with coronary heart disease (described in "Can You Catch a Heart Attack?" by P. Brown, *New Scientist*, June 1996, p. 38–42). Furthermore, a high proportion of patients with acute myocardial infarction also had an acute *C. pneumoniae* infection (F. Blasi et al., "A Possible Role for *Chlamydia pneumoniae* Infection in Acute Myocardial Infarction Onset", Abstracts from the Third European Chlamydia Meeting, Sep. 11–14, 1996, Vienna, Austria, p. 220). These and other results have generated interest in the diagnosis of infection by Chlamydia species.

The life cycle of Chlamydia species, particularly of *Chlamydia pneumoniae*, increases the difficulty of detecting these bacteria. Essentially, these bacteria have two parts in their life cycle. In one part, these bacteria enter a host cell and live as an intracellular reticular body. In the second part, the bacteria leave the host cell and live as an extracellular elementary body. Thus, the bacteria can "hide" within the host cell, inaccessible to the immune system of the host, and then leave the host cell in order to infect other tissues of the host. Since the entrance of the bacteria into the host cell requires an alteration in the integrity of the latter cell membrane, such an infection of individual host cells could cause a lesion in the host tissue. Thus, not only does such an infection make Chlamydia species harder to detect, it also could lead directly to damage of the host tissue, such as a coronary artery. Clearly, rapid, accurate and non-invasive methods of detection of Chlamydia species are necessary.

Unfortunately, currently available methods to diagnose an infection by a Chlamydia species, particularly by *Chlamydia pneumoniae*, are invasive and difficult to perform, and cannot measure Chlamydia activity in "real time". That is, there is a significant delay between the time the Chlamydia activity takes place, and the time such activity is measured by the test.

For example, PCT Patent No. 9222819 to Kuo (hereinafter referred to as "Kuo") discloses a method of detecting a first marker associated with *Chlamydia pneumoniae* in a biological sample, and of detecting a second marker associated with arterial granuloma in the same sample. The Chlamydia marker includes the concentration of lipids from *Chlamydia pneumoniae* in a serum or tissue sample. Such a method has the disadvantage of requiring a serum or tissue sample, both of which are biohazards. Furthermore, this test examines two markers, which requires two separate measurements. Certain of these measurements are made in a static sample in vitro, rather than being made in real time in vivo. Thus, the concentration of such a marker is not necessarily proportional to the actual activity of Chlamydia bacteria in a subject, and more importantly, a significant delay must take place between the time the activity takes place, and the time the measurement is made.

Examples of such markers include antibodies raised against, and lipids released from, *Chlamydia pneumoniae*. The disadvantage of these types of markers is that they do not reflect current activity of the bacteria. The presence of antibodies, for example, can indicate a current infection, or an infection which occurred and was resolved previously. Thus, it is difficult to determine the level of the present activity of the bacteria, if any.

Those markers which are described as being measured in vivo have other disadvantages. For example, the disclosure mentions a radiolabelled antibody against *Chlamydia pneumoniae* which is delivered through a catheter to the heart. This procedure is very invasive and does not allow the level of bacteria to be easily measured, since the antibody would not necessarily be able to bind to bacteria in the intracellular portion of their life cycle. Furthermore, such a procedure also cannot directly measure the level of activity of the bacteria themselves in real time.

PCT Patent No. 9000061 to Saikku discloses a method of detecting the presence of Chlamydia in vitro by using a sample of blood, urine or tissue biopsy from the heart. Obtaining a tissue biopsy is clearly invasive, and thus disadvantageous. Even using a urine sample is somewhat disadvantageous, since it requires handling of a bodily fluid which is potentially biohazardous. Furthermore, this method uses antibodies to detect Chlamydial antigens, or alternatively measures the level of antibodies against Chlamydia, rather than measuring the activity of the bacteria themselves. Not only is such a method indirect, but it also creates a delay between the time the Chlamydia activity occurs in the subject, and the time the measurement is made. Also, the presence of antibodies indicates only that an infection by Chlamydia species occurred at some point in the past, not that such an infection is current. Furthermore, no mention is made of an in vivo method of measurement. Thus, all of the currently available methods of diagnosing Chlamydia species are disadvantageous.

However, rapid and non-invasive methods of detecting infection by *Helicobacter pylori* in the gastrointestinal tract have been described. These methods involve administering a substrate to a subject and then analyzing the exhaled breath of the subject for the presence of a hydrolysis product or products, which indicate the presence of *Helicobacter pylori* in the gastrointestinal tract. For example, U.S. Pat. No. 4,830,010 to Marshall (hereinafter referred to as "Marshall") describes a method of detecting *Helicobacter pylori* by orally administering isotopically-labelled urea to a subject. *Helicobacter pylori* produces a large quantity of the enzyme urease, which hydrolyzes urea to form carbon dioxide and ammonia. Either one or both of these hydrolysis products can have the isotopic label. At least one isotopically-labelled product is then exhaled by the subject and can be detected in the exhaled breath of the subject by an appropriate measuring instrument. Thus, the breath test for diagnosing *Helicobacter pylori* is rapid, easy to perform and relatively non-invasive. Unfortunately, no such breath test is currently available for the diagnosis of Chlamydia species.

There is thus a widely recognized need for, and it would be highly advantageous to have, a breath test for the detection of Chlamydia species in a subject, which is relatively non-invasive, and which can measure the activity of Chlamydia bacteria with relatively little delay.

SUMMARY OF THE INVENTION

According to the present invention there is provided a method for the diagnosis of Chlamydia species in a subject, comprising the steps of: (a) administering a substrate to the subject, the substrate being cleavable by an enzyme of Chlamydia species to form a cleavage product; and (b) analyzing exhaled breath of the subject after a suitable time period for a concentration of the cleavage product, the concentration indicating activity of the Chlamydia species in the subject. Preferably, the Chlamydia species is selected from the group consisting of *Chlamydia pneumoniae, Chlamydia psittaci* and *Chlamydia trachomatis*. Most preferably, the Chlamydia species is *Chlamydia pneumoniae*. Also preferably, the exhaled breath of the subject is analyzed by an infrared spectrometer. Preferably, the substrate is isotopically-labelled. Also preferably, the cleavage product is carbon dioxide, most preferably carbon-13 isotopically-labelled carbon dioxide.

According to further features in preferred embodiments of the invention described below, there is provided a breath test kit for diagnosing Chlamydia species in a subject, comprising a substrate for administering to the subject, the substrate being cleavable by an enzyme of the Chlamydia species to form a cleavage product, the cleavage product being present in exhaled breath of the subject.

DESCRIPTION OF THE PREFERRED EMBODIMENTS

The present invention is of a breath test which can be used to detect the presence of Chlamydia species in a subject. Specifically, the present invention can be used to diagnose the presence of Chlamydia species by administering a substrate to a subject and then detecting the concentration of a cleavage product or products in the exhaled breath of the subject. The concentration of the cleavage product or products indicates the level of activity of Chlamydia species in the subject, which can be used to diagnose Chlamydia species in the subject. Hereinafter, the term "Chlamydia species" is defined as those bacteria which belong to the Chlamydia genus including, but not limited to, *Chlamydia trachomatis, Chlamydia psittaci* and *Chlamydia pneumoniae*.

EXAMPLE 1

Method of Diagnosing Chlamydia Species in a Subject

The method of diagnosing Chlamydia species in a subject is performed as follows. First, a safe and effective amount of a substrate, preferably appropriately labelled, is administered to the subject. Second, after a suitable time period, the exhaled breath of the subject is analyzed to detect the concentration of a cleavage product or products, produced when an enzyme from Chlamydia bacteria cleaves the substrate. By "cleaves" it is meant that the enzyme can break at least one chemical bond of the substrate, forming a plurality of products, by a chemical process including, but not limited to, hydrolysis. A product so formed is a "cleavage product". The concentration of the cleavage product or products indicates the level of activity of Chlamydia species in the subject, which can be used to determine a diagnosis of Chlamydia species. A positive diagnosis indicates that a Chlamydia species is present in the subject, constituting an infection of the subject by the Chlamydia species. Such a method for diagnosis can also be referred to as a "breath test".

Hereinafter, the term "subject" refers to a human or lower animal on whom the method of diagnosing Chlamydia species is performed.

The term "suitable time period" refers to the length of time required for a cleavage product or products to form and to be exhaled in the breath of the subject. Thus, the requisite time permits a number of events to occur. First, the substrate must be absorbed by the subject. Next, the substrate must be accessible to Chlamydia species, or a part thereof such as an enzyme, which may be present in the subject. Then, the substrate must be cleaved by an enzyme of Chiamydia species to form a cleavage product or products. Finally, the cleavage product or products must be exhaled in the breath of the subject.

The term "safe and effective amount of substrate" refers to an amount of a substrate which is sufficient to produce a detectable level of a cleavage product or products, without an untoward level of adverse side effects, such as toxicity, irritation, allergy or hypersensitivity responses. The level of any such side effects should be commensurate with acceptable risk/benefit ratios.

Examples of appropriate labels for the substrate, and hence for the cleavage product or products, are those which can be detected by an appropriate measuring instrument, but which are substantially not harmful or toxic to the subject including, but not limited to, carbon-13 or carbon-14, oxygen-18 or nitrogen-15, isotope-labelling. An isotope is a form of an element, such as carbon, with a specific mass. For example, carbon-12 has a mass of 12 atomic mass units. The term "isotope-labelling" means that the naturally more abundant isotope of each of these elements is at least partially replaced by a less abundant isotope. For example, the naturally more abundant carbon-12 atoms could be at least partially replaced by the less abundant carbon-13 atoms, permitting the cleavage product or products which carry the label to be more easily detected, since the less abundant isotope can be distinguished from the naturally more abundant isotope. Furthermore, the advantage of certain isotopes such as carbon-13 is that they are stable, so that they are not radioactive, unlike isotopes such as carbon-14. Therefore, preferably stable, non-radioactive isotopes such as carbon-13 are used as labels.

By the term "administered", it is meant that a method in accordance with good medical practice is used to introduce the substrate into the subject. The substrate can be administered to a subject in a number of ways, which are well known in the art. For example, administration may be done topically (including ophtalmically, vaginally, rectally, intranasally), orally, by inhalation, or parenterally, for example by intravenous drip or intraperitoneal, subcutaneous, or intramuscular injection. Most preferably, administration is done orally, topically or by inhalation, as these methods are relatively non-invasive.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

Following the step of administering the labelled substrate to the subject, the exhaled breath of the subject is analyzed to detect a cleavage product or products, which indicate the presence of Chlamydia species. The product or products are detected by analyzing a gas sample of the exhaled breath of the subject with a measuring instrument. Such a gas sample can be obtained in a number of ways including, but not limited to, having the subject exhale or blow into a tube connected to the measuring instrument.

The type of measuring instrument used to detect the product or products depends upon the type of label. For example, if a carbon-13 isotopically-labelled substrate is used, the carbon-13 isotopically-labelled cleavage product or products can be detected by using a measuring instrument including, but not limited to a mass spectrometer or a gas analyzer, which is sensitive to the carbon-13 isotope. The ratio of the concentration of carbon-13 isotopically-labelled cleavage product or products to the concentration of carbon-12 cleavage product or products is then determined. Since carbon-12 is the more abundant isotope in nature, carbon-12 atoms are more abundant in unlabelled molecules. Thus, a higher carbon-13/carbon-12 ratio indicates a higher concentration of the carbon-13 isotopically-labelled cleavage product or products, which positively indicates the presence of Chlamydia species in the subject.

Preferably, at least one of the cleavage products is carbon-13 isotopically-labelled carbon dioxide. Examples of measuring instruments which can be used with carbon-13 isotopically-labelled carbon dioxide include, but are not limited to, an infrared spectrometer. These infrared spectrometers are well known in the art, and have the advantage of being both rapid and accurate. Examples of such infrared spectrometers are disclosed in U.S. Pat. No. 5,063,275, herein incorporated by reference.

Alternatively and preferably, at least one of the cleavage products is nitrogen-15 isotopically-labelled ammonia. Of course, both carbon-13 isotopically-labelled carbon dioxide and nitrogen-15 isotopically-labelled ammonia could be present, providing that the substrate has both labels. Both ammonia and carbon dioxide have the advantage of being molecules which are present in the exhaled breath of the subject.

The substrate itself must be cleavable by an enzyme of Chlamydia species. A "cleavable substrate" is one which is cleaved by the enzyme to form a plurality of products, referred to as "cleavage products". One example of such an enzyme has been described by K. H. Valkonen and P. Saikku [Abstracts from the Third European Chlamydia Meeting, Sep. 11–14, 1996, Vienna, Austria, p. 41]. This enzyme is a cysteine proteinase known as K7, found in *Chlamydia pneumoniae*. The term "cysteine proteinase" means that K7 cleaves proteins at cysteine amino acid residues. K7 may be involved in the pathogenicity of *Chlamydia pneumoniae,* since K7 may be the proteinase which allows the bacterium to enter the host cell during the intracellular part of the bacterial life cycle. Thus, the level of activity of the K7 enzyme may even indicate the pathogenicity of *Chlamydia pneumoniae.*

The K7 enzyme has been specifically demonstrated to cleave gelatin and casein, both of which are naturally occurring proteins used in foodstuffs and which are therefore substantially non-toxic.

However, a suitable substrate for this enzyme would not necessarily need to be a polypeptide. Indeed, for ease of absorption by the subject and presentation to the Chlamydia species, non-polypeptidic substrates could be more convenient. One example of such a substrate is L-leucine p-nitro anilide [K. H. Valkonen and P. Saikku, poster presented at the Third European Chlamydia Meeting, Sep. 11–14, 1996, Vienna, Austria]. Such a substrate could also preferably be isotopically-labelled by synthesizing leucine molecules which are carbon-13 isotopically-labelled or nitrogen-15 isotopically-labelled, for example, and then preparing L-leucine p-nitro anilide from these labelled molecules.

One further required characteristic of the substrate is that at least one of its cleavage products must be present in the exhaled breath of the subject. Examples of molecules which are present in exhaled breath include, but are not limited to, ammonia and carbon dioxide. Therefore, preferably at least one of the cleavage products is ammonia or carbon dioxide.

Such a breath test for Chlamydia species has a number of advantages. First, analyzing the exhaled breath of a subject is inherently non-invasive, since the subject must simply blow or exhale air so that a measuring instrument can detect the presence of a cleavage product or products. Second, because the cleavage product or products reflects the actual activity of an enzyme within Chlamydia bacteria, the concentration of such a product or products reflects the actual activity of Chlamydia bacteria within a subject. Third, the exhaled breath of the subject can be analyzed in real time; that is, there is relatively little delay between the time the Chlamydia activity takes place, and the time such activity is measured. Thus, such a breath test clearly has a number of advantages over previously known Chlamydia tests.

EXAMPLE 2

Breath Test Kit for Diagnosing Chlamydia

As described in Example 1 above, Chlamydia species can be diagnosed in a subject by using a breath test. A breath test kit to diagnose Chlamydia species in a subject would include an item or items necessary for performing at least one of the methods described in Example 1. For example, such a breath test kit could include a substrate to be administered to the subject. Such substrates include, but are not limited to, those described in Example 1 above.

As another example, the breath test kit could include, in addition to the substrate, a device for administering the substrate to the subject. For example, if the substrate is to be inhaled, such a device could be an inhalation device of the type used to administer medications to patients with asthma. Alternatively, if the substrate is to be administered orally, such a device could be a metered-dose syringe for oral administration, for example.

While the invention has been described with respect to a limited number of embodiments, it will be appreciated that many variations, modifications and other applications of the invention may be made.

What is claimed is:

1. A method for the diagnosis of Chlamydia species in a subject, comprising the steps of:
   (a) administering a substrate to the subject, said substrate being cleavable by an enzyme of the Chlamydia species to form a cleavage product; and
   (b) analyzing exhaled breath of the subject after a suitable time period for a concentration of said cleavage product, said concentration indicating current activity of the Chlamydia species in the subject.

2. The method of claim 1, wherein said Chlamydia species is selected from the group consisting of *Chlamydia pneumoniae, Chlamydia psittaci* and *Chlamydia trachomatis.*

3. The method of claim 2, wherein said Chlamydia species is *Chlamydia pneumoniae.*

4. The method of claim 1 and wherein said analyzing exhaled breath of the subject comprises analyzing using a measuring instrument selected from the group consisting of an infrared spectrometer and a mass spectrometer.

5. The method of claim 1 further comprising isotopically labeling said substrate.

6. The method of claim 5, wherein said cleavage product is carbon dioxide.

7. The method of claim 6 further comprising analyzing said carbon dioxide for carbon-13 isotopically-labeled content.

8. The method of claim 5, wherein said cleavage product is ammonia.

9. The method of claim 8 further comprising analyzing said ammonia for nitrogen-13 isotopically-labeled content.

10. The method according to claim 1 further comprising isotopically labeling said cleavage product.

11. A test kit for diagnosing Chlamydia species in subject using a breath test, comprising a substrate for administering to the subject, said substrate being cleavable by an enzyme of the Chlamydia species to form a cleavage product, said cleavage product being present in exhaled breath of the subject and indicating current activity of the Chlamydia species in the subject.

12. The test kit of claim 11, wherein the Chlamydia species is selected from the group consisting of *Chlamydia pneumoniae, Chlamydia psittaci* and *Chlamydia trachomatis.*

13. The test kit of claim 12, wherein the Chlamydia species is *Chlamydia pneumoniae.*

14. The test kit of claim 12, wherein said substrate is isotopically-labelled.

15. The test kit of claim 10 wherein said substrate is isotopically labelled.

16. The test kit of claim 10 wherein said cleavage product is isotopically labelled.

* * * * *